United States Patent
Fix

(10) Patent No.: US 10,092,357 B2
(45) Date of Patent: *Oct. 9, 2018

(54) TAPERED LIQUID LIGHT GUIDE

(71) Applicant: The Spectranetics Corporation, Colorado Springs, CO (US)

(72) Inventor: Clint Fix, Grand Junction, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/138,949

(22) Filed: Apr. 26, 2016

(65) Prior Publication Data

US 2016/0310214 A1 Oct. 27, 2016

Related U.S. Application Data

(63) Continuation of application No. 14/613,949, filed on Feb. 4, 2015, now Pat. No. 9,339,337, which is a
(Continued)

(51) Int. Cl.
*A61B 18/24* (2006.01)
*A61B 18/20* (2006.01)
*A61B 18/00* (2006.01)

(52) U.S. Cl.
CPC ............ *A61B 18/24* (2013.01); *A61B 18/245* (2013.01); *A61B 2018/00577* (2013.01); *A61B 2018/206* (2013.01)

(58) Field of Classification Search
CPC .................. A61B 18/24; A61B 18/245; A61B 2018/00577; A61B 2018/206
See application file for complete search history.

(56) References Cited

U.S. PATENT DOCUMENTS 2,667,324 A   1/1954   Hansen
2,828,744 A *   4/1958   Hirsch ............... A61M 5/329
                                                                       604/165.01

(Continued)

FOREIGN PATENT DOCUMENTS

EP    0257811 A2   3/1988
EP    0342505 B1   11/1989
(Continued)

OTHER PUBLICATIONS

Ghosh et al. (Journal of Sensor Technology, 2012;2:48-54).*
(Continued)

*Primary Examiner* — Ernst V Arnold

(57) ABSTRACT

A catheter tip is provided according to various embodiments of the disclosure. The catheter tip may comprise a distal end, a proximal end, and tubular walls. The distal end includes a distal aperture with a distal inside diameter, and the proximal end includes a proximal aperture with a proximal inside diameter. The proximal inside diameter may be greater than the distal inside diameter. The proximal end comprises attachment means configured to couple the proximal end with a distal end of a laser catheter. The tubular walls may include at least an inside taper from the proximal end to the distal end such that the inner tubular walls generally taper from the proximal inside diameter to the distal inside diameter. Moreover, the tubular walls may be configured to direct at least a liquid medium, for example, a biocompatible solution, toward the distal aperture.

19 Claims, 6 Drawing Sheets

Related U.S. Application Data continuation of application No. 12/176,886, filed on Jul. 21, 2008, now Pat. No. 8,979,828.

(56) References Cited

U.S. PATENT DOCUMENTS

| | | | |
|---|---|---|---|
| 2,987,292 | A | 6/1961 | Barkell et al. |
| 3,585,996 | A | 6/1971 | Pannier, Jr. et al. |
| 4,013,080 | A | 3/1977 | Froning |
| 4,053,845 | A | 10/1977 | Gould |
| 4,143,853 | A | 3/1979 | Abramson |
| 4,243,034 | A | 1/1981 | Brandt |
| 4,264,020 | A | 4/1981 | Loiseau |
| 4,274,408 | A | 6/1981 | Nimrod |
| 4,333,455 | A | 6/1982 | Bodicky |
| 4,417,886 | A | 11/1983 | Frankhouser et al. |
| 4,468,224 | A | 8/1984 | Enzmann et al. |
| 4,525,157 | A | 6/1985 | Vaillancourt |
| 4,540,411 | A | 9/1985 | Bodicky |
| 4,564,011 | A * | 1/1986 | Goldman ............. A61B 17/12 606/15 |
| 4,641,912 | A | 2/1987 | Goldenberg |
| 4,655,750 | A | 4/1987 | Vaillancourt |
| 4,686,979 | A | 8/1987 | Gruen et al. |
| 4,732,448 | A | 3/1988 | Goldenberg |
| 4,747,405 | A | 5/1988 | Leckrone |
| 4,768,709 | A | 9/1988 | Yie |
| 4,784,132 | A | 11/1988 | Fox et al. |
| 4,789,104 | A | 12/1988 | Anderson |
| 4,799,754 | A | 1/1989 | Goldenberg |
| 4,807,620 | A | 2/1989 | Strul et al. |
| 4,809,710 | A | 3/1989 | Williamson |
| 4,830,460 | A | 5/1989 | Goldenberg |
| 4,842,591 | A | 6/1989 | Luther |
| 4,844,062 | A | 7/1989 | Wells |
| 4,848,336 | A | 7/1989 | Fox et al. |
| 4,857,062 | A | 8/1989 | Russell |
| 4,860,742 | A | 8/1989 | Park et al. |
| 4,863,431 | A | 9/1989 | Vaillancourt |
| 4,924,863 | A | 5/1990 | Sterzer |
| 4,932,413 | A | 6/1990 | Shockey et al. |
| 4,960,411 | A | 10/1990 | Buchbinder |
| 4,966,588 | A | 10/1990 | Rayman et al. |
| 4,973,329 | A | 11/1990 | Park et al. |
| 4,978,341 | A | 12/1990 | Niederhauser |
| 5,007,901 | A | 4/1991 | Shields |
| 5,011,472 | A | 4/1991 | Aebischer et al. |
| 5,011,473 | A | 4/1991 | Gatturna |
| 5,016,964 | A | 5/1991 | Donnelly |
| 5,041,108 | A | 8/1991 | Fox et al. |
| 5,045,065 | A | 9/1991 | Raulerson |
| 5,053,013 | A | 10/1991 | Ensminger et al. |
| 5,070,882 | A | 12/1991 | Bui et al. |
| 5,085,645 | A | 2/1992 | Purdy et al. |
| 5,097,841 | A | 3/1992 | Moriuchi et al. |
| 5,098,396 | A | 3/1992 | Taylor et al. |
| 5,112,328 | A | 5/1992 | Taboada et al. |
| 5,116,323 | A | 5/1992 | Kreuzer et al. |
| 5,125,903 | A | 6/1992 | McLaughlin et al. |
| 5,158,560 | A | 10/1992 | Sogawa et al. |
| 5,159,861 | A | 11/1992 | Anderson |
| 5,178,153 | A | 1/1993 | Einzig |
| 5,179,861 | A | 1/1993 | Asano et al. |
| 5,188,632 | A | 2/1993 | Goldenberg |
| 5,195,978 | A | 3/1993 | Schiffer |
| 5,226,879 | A | 7/1993 | Ensminger et al. |
| 5,240,004 | A | 8/1993 | Walinsky et al. |
| 5,246,437 | A | 9/1993 | Abela |
| 5,250,045 | A | 10/1993 | Bohley |
| 5,250,069 | A | 10/1993 | Nobuyoshi et al. |
| 5,263,953 | A | 11/1993 | Bagby |
| 5,267,341 | A * | 11/1993 | Shearin ............. A61B 18/24 385/125 |
| 5,273,042 | A | 12/1993 | Lynch et al. |
| 5,281,199 | A | 1/1994 | Ensminger et al. |
| 5,295,969 | A | 3/1994 | Fischell et al. |
| 5,304,171 | A | 4/1994 | Gregory et al. |
| 5,308,318 | A | 5/1994 | Plassche et al. |
| 5,325,746 | A | 7/1994 | Anderson |
| 5,334,187 | A | 8/1994 | Fischell et al. |
| 5,350,375 | A | 9/1994 | Deckelbaum et al. |
| 5,352,197 | A | 10/1994 | Hammersmark et al. |
| 5,366,441 | A | 11/1994 | Crawford |
| 5,395,348 | A | 3/1995 | Ryan |
| 5,397,310 | A | 3/1995 | Chu et al. |
| 5,415,653 | A | 5/1995 | Wardle et al. |
| 5,417,699 | A | 5/1995 | Klein et al. |
| 5,429,604 | A | 7/1995 | Hammersmark et al. |
| 5,429,617 | A | 7/1995 | Hammersmark et al. |
| 5,440,664 | A | 8/1995 | Harrington et al. |
| 5,454,782 | A | 10/1995 | Perkins |
| 5,456,284 | A | 10/1995 | Ryan et al. |
| 5,456,680 | A | 10/1995 | Taylor et al. |
| 5,468,239 | A | 11/1995 | Tanner et al. |
| 5,470,330 | A | 11/1995 | Goldenberg et al. |
| 5,484,433 | A | 1/1996 | Taylor et al. |
| 5,489,274 | A | 2/1996 | Chu et al. |
| 5,497,782 | A | 3/1996 | Fugoso |
| 5,501,227 | A | 3/1996 | Yock |
| 5,501,671 | A | 3/1996 | Rosen et al. |
| 5,514,128 | A | 5/1996 | Hillsman et al. |
| 5,520,665 | A | 5/1996 | Fleetwood |
| 5,537,499 | A | 7/1996 | Brekke |
| 5,540,236 | A | 7/1996 | Ginn |
| 5,571,151 | A | 11/1996 | Gregory |
| 5,573,516 | A | 11/1996 | Tyner |
| 5,573,531 | A | 11/1996 | Gregory |
| 5,607,419 | A | 3/1997 | Amplatz et al. |
| 5,613,663 | A | 3/1997 | Schmidt et al. |
| 5,623,940 | A | 4/1997 | Daikuzono |
| 5,643,251 | A | 7/1997 | Hillsman et al. |
| 5,649,923 | A * | 7/1997 | Gregory ............. A61B 18/24 606/14 |
| 5,685,862 | A | 11/1997 | Mahurkar |
| 5,702,367 | A | 12/1997 | Cover et al. |
| 5,704,914 | A | 1/1998 | Stocking et al. |
| 5,722,972 | A | 3/1998 | Power et al. |
| 5,749,861 | A | 5/1998 | Guala et al. |
| 5,769,843 | A | 6/1998 | Abela et al. |
| 5,817,144 | A | 10/1998 | Gregory |
| 5,820,596 | A | 10/1998 | Rosen et al. |
| 5,824,026 | A | 10/1998 | Diaz |
| 5,827,234 | A | 10/1998 | Loos et al. |
| 5,836,946 | A | 11/1998 | Diaz et al. |
| 5,843,046 | A | 12/1998 | Motisi et al. |
| RE36,104 | E | 2/1999 | Solar |
| 5,865,801 | A | 2/1999 | Houser |
| 5,879,338 | A | 3/1999 | Mahurkar |
| 5,921,970 | A | 7/1999 | Vandenberg |
| 5,968,036 | A | 10/1999 | Goodman et al. |
| 5,976,124 | A | 11/1999 | Reiser |
| 5,980,492 | A | 11/1999 | Rosen et al. |
| 5,989,223 | A | 11/1999 | Chu et al. |
| 5,989,243 | A | 11/1999 | Goldenberg |
| 5,989,700 | A | 11/1999 | Krivopal |
| 5,993,443 | A | 11/1999 | Murphy-Chutorian et al. |
| 6,007,522 | A | 12/1999 | Agro et al. |
| 6,022,342 | A | 2/2000 | Mukherjee |
| 6,039,726 | A | 3/2000 | Lewis et al. |
| 6,066,130 | A | 5/2000 | Gregory et al. |
| 6,096,009 | A | 8/2000 | Windheuser et al. |
| 6,117,128 | A | 9/2000 | Gregory |
| 6,152,910 | A | 11/2000 | Agro et al. |
| 6,156,029 | A | 12/2000 | Mueller |
| 6,163,641 | A | 12/2000 | Eastgate |
| 6,165,215 | A | 12/2000 | Rottenberg et al. |
| 6,176,852 | B1 | 1/2001 | Ischinger |
| 6,196,230 | B1 | 3/2001 | Hall et al. |
| 6,197,001 | B1 | 3/2001 | Wilson et al. |
| 6,235,001 | B1 | 5/2001 | O'Holloran et al. |
| 6,271,621 | B1 | 8/2001 | Ito et al. |
| 6,287,280 | B1 | 9/2001 | Lampropoulos et al. |
| 6,290,668 | B1 | 9/2001 | Gregory et al. |
| 6,290,710 | B1 | 9/2001 | Cryer et al. |
| 6,312,404 | B1 | 11/2001 | Agro et al. |

(56) References Cited

U.S. PATENT DOCUMENTS

| | | |
|---|---|---|
| 6,315,753 B1 | 11/2001 | Cragg et al. |
| 6,346,093 B1 | 2/2002 | Allman et al. |
| 6,458,098 B1 | 10/2002 | Kanesaka |
| 6,488,667 B1 | 12/2002 | Murphy |
| 6,488,674 B2 | 12/2002 | Becker et al. |
| 6,491,647 B1 | 12/2002 | Bridger et al. |
| 6,520,951 B1 | 2/2003 | Carrillo et al. |
| 6,551,302 B1 | 4/2003 | Rosinko et al. |
| 6,572,590 B1 | 6/2003 | Stevens et al. |
| 6,572,791 B2 | 6/2003 | Sakata et al. |
| 6,582,401 B1 | 6/2003 | Windheuser et al. |
| 6,606,515 B1 | 8/2003 | Windheuser et al. |
| 6,663,597 B1 | 12/2003 | Windheuser et al. |
| 6,694,983 B2 | 2/2004 | Wolf et al. |
| 6,743,208 B1 | 6/2004 | Coyle |
| 6,746,442 B2 | 6/2004 | Agro et al. |
| 6,763,722 B2 | 7/2004 | Fjield et al. |
| 6,808,498 B2 | 10/2004 | Laroya et al. |
| 6,869,416 B2 | 3/2005 | Windheuser et al. |
| 6,879,854 B2 | 4/2005 | Windheuser et al. |
| 6,886,411 B2 | 5/2005 | Kjellman et al. |
| 6,963,688 B2 | 11/2005 | Nath |
| 6,974,422 B1 | 12/2005 | Millar |
| 6,994,695 B1 | 2/2006 | Millar |
| 6,997,908 B2 | 2/2006 | Carrillo et al. |
| 7,008,404 B2 | 3/2006 | Nakajima |
| 7,025,746 B2 | 4/2006 | Tal |
| 7,060,052 B2 | 6/2006 | Windheuser et al. |
| 7,076,285 B2 | 7/2006 | Windheuser et al. |
| 7,172,577 B2 | 2/2007 | Mangano et al. |
| 7,179,252 B2 | 2/2007 | Agro et al. |
| 7,241,285 B1 | 7/2007 | Dikeman |
| 7,261,703 B2 | 8/2007 | Lampropoulos et al. |
| 7,355,182 B2 | 4/2008 | Szu |
| 7,396,343 B2 | 7/2008 | Brown |
| 7,544,184 B2 | 6/2009 | Cope et al. |
| 7,544,193 B2 | 6/2009 | Agro et al. |
| 7,578,814 B2 | 8/2009 | Accisano et al. |
| 7,615,033 B2 | 11/2009 | Leong |
| 7,678,129 B1 | 3/2010 | Gesswein et al. |
| 7,682,340 B2 | 3/2010 | Funamura et al. |
| 7,706,861 B2 | 4/2010 | Windheuser et al. |
| 7,708,721 B2 | 5/2010 | Khaw |
| 7,722,567 B2 | 5/2010 | Tal |
| 7,760,316 B2 | 7/2010 | Hirakata et al. |
| 7,766,049 B2 * | 8/2010 | Miller ............... A61M 25/005 138/116 |
| 7,819,844 B2 | 10/2010 | Spenser et al. |
| 7,846,133 B2 | 12/2010 | Windheuser et al. |
| 7,909,811 B2 | 3/2011 | Agro et al. |
| 7,918,859 B2 | 4/2011 | Katoh et al. |
| 8,006,953 B2 | 8/2011 | Bennett |
| 8,043,208 B2 | 10/2011 | Windheuser et al. |
| 8,052,647 B2 | 11/2011 | Raulerson et al. |
| 8,066,669 B2 | 11/2011 | Christensen et al. |
| 8,066,670 B2 | 11/2011 | Cluff et al. |
| 8,066,679 B2 | 11/2011 | Hwang |
| 8,083,690 B2 | 12/2011 | Peterson et al. |
| 8,105,286 B2 | 1/2012 | Anderson et al. |
| 8,128,598 B2 | 3/2012 | Uihlein |
| 8,177,760 B2 | 5/2012 | Rome et al. |
| 8,202,251 B2 | 6/2012 | Bierman et al. |
| 8,202,254 B2 | 6/2012 | Schweikert et al. |
| 8,206,283 B2 | 6/2012 | Windheuser et al. |
| 8,206,375 B2 | 6/2012 | Snow |
| 8,211,087 B2 | 7/2012 | Carter et al. |
| 8,216,295 B2 | 7/2012 | Benjamin et al. |
| 8,257,382 B2 | 9/2012 | Rottenberg et al. |
| 8,257,383 B2 | 9/2012 | Rottenberg et al. |
| 8,979,828 B2 | 3/2015 | Fix |
| 9,066,742 B2 | 6/2015 | Splinter |
| 9,162,038 B2 | 10/2015 | Rottenberg et al. |
| 9,289,173 B2 | 3/2016 | Splinter |
| 9,339,337 B2 | 5/2016 | Fix |
| 9,421,065 B2 | 8/2016 | Splinter et al. |
| 2001/0003790 A1 | 6/2001 | Ben-Haim et al. |
| 2001/0034501 A1 | 10/2001 | Tom |
| 2002/0026188 A1 | 2/2002 | Balbierz et al. |
| 2002/0068885 A1 | 6/2002 | Harhen et al. |
| 2002/0072647 A1 | 6/2002 | Schock et al. |
| 2002/0188313 A1 | 12/2002 | Johnson et al. |
| 2003/0051733 A1 | 3/2003 | Kotmel et al. |
| 2003/0216685 A1 | 11/2003 | Porter |
| 2004/0060362 A1 | 4/2004 | Kjellmann et al. |
| 2004/0079429 A1 | 4/2004 | Miller et al. |
| 2004/0131299 A1 | 7/2004 | Adoram et al. |
| 2004/0199156 A1 | 10/2004 | Rioux et al. |
| 2004/0215146 A1 | 10/2004 | Lampropoulos et al. |
| 2005/0131289 A1 | 6/2005 | Aharoni et al. |
| 2005/0143770 A1 | 6/2005 | Carter et al. |
| 2005/0148925 A1 | 7/2005 | Rottenberg et al. |
| 2005/0159770 A1 | 7/2005 | Divani et al. |
| 2005/0192637 A1 | 9/2005 | Girouard et al. |
| 2005/0251116 A1 | 11/2005 | Steinke et al. |
| 2006/0013533 A1 | 1/2006 | Slatkine |
| 2006/0020241 A1 | 1/2006 | Piskun et al. |
| 2006/0079813 A1 | 4/2006 | Schlumpf |
| 2006/0235314 A1 | 10/2006 | Migliuolo et al. |
| 2006/0264834 A1 | 11/2006 | Vaillancourt |
| 2007/0118079 A1 | 5/2007 | Moberg et al. |
| 2007/0162071 A1 | 7/2007 | Burkett et al. |
| 2007/0233185 A1 | 10/2007 | Anderson et al. |
| 2007/0270931 A1 | 11/2007 | Leanna et al. |
| 2008/0159825 A1 | 7/2008 | Tegg |
| 2008/0161794 A1 | 7/2008 | Wang et al. |
| 2008/0234567 A1 | 9/2008 | Tearney et al. |
| 2008/0243065 A1 | 10/2008 | Rottenberg et al. |
| 2008/0243067 A1 | 10/2008 | Rottenberg et al. |
| 2008/0300574 A1 | 12/2008 | Belson et al. |
| 2008/0300662 A1 | 12/2008 | Taylor |
| 2008/0306499 A1 | 12/2008 | Katoh et al. |
| 2009/0005754 A1 | 1/2009 | Soetermans |
| 2009/0221961 A1 | 9/2009 | Tal et al. |
| 2009/0254074 A1 | 10/2009 | Splinter et al. |
| 2009/0292253 A1 | 11/2009 | Raulerson et al. |
| 2010/0016842 A1 | 1/2010 | Fix |
| 2010/0094310 A1 | 4/2010 | Warring et al. |
| 2010/0137892 A1 | 6/2010 | Krolik et al. |
| 2011/0021994 A1 | 1/2011 | Anderson et al. |
| 2011/0060315 A1 | 3/2011 | Windheuser et al. |
| 2011/0077621 A1 | 3/2011 | Graham et al. |
| 2011/0144572 A1 | 6/2011 | Kassab et al. |
| 2011/0196344 A1 | 8/2011 | Agro et al. |
| 2011/0251559 A1 | 10/2011 | Tal et al. |
| 2011/0270192 A1 | 11/2011 | Anderson et al. |
| 2011/0276002 A1 | 11/2011 | Bierman |
| 2011/0282285 A1 | 11/2011 | Blanchard et al. |
| 2012/0041371 A1 | 2/2012 | Tal et al. |
| 2012/0184896 A1 | 7/2012 | DeLegge et al. |
| 2012/0220942 A1 | 8/2012 | Hall et al. |
| 2012/0265229 A1 | 10/2012 | Rottenberg et al. |
| 2012/0265233 A1 | 10/2012 | Waisman et al. |
| 2013/0165867 A1 | 6/2013 | Isaacson et al. |
| 2015/0148790 A1 | 5/2015 | Fix |
| 2015/0245796 A1 | 9/2015 | Splinter |
| 2016/0000454 A1 | 1/2016 | Rottenberg et al. |
| 2016/0183844 A1 | 6/2016 | Splinter |
| 2016/0354149 A1 | 12/2016 | Splinter et al. |

FOREIGN PATENT DOCUMENTS

| | | |
|---|---|---|
| EP | 0388112 B1 | 9/1990 |
| EP | 0623673 A2 | 11/1994 |
| EP | 0633184 A1 | 1/1995 |
| EP | 0650666 A1 | 5/1995 |
| EP | 0724098 A1 | 7/1996 |
| EP | 0846064 A1 | 6/1998 |
| EP | 0897295 A1 | 2/1999 |
| EP | 1035880 A1 | 9/2000 |
| EP | 1045708 A1 | 10/2000 |
| EP | 1098671 A1 | 5/2001 |
| EP | 1109590 A1 | 6/2001 |
| EP | 1399549 A1 | 3/2004 |
| EP | 1441672 A1 | 8/2004 |

(56) References Cited

FOREIGN PATENT DOCUMENTS

| EP | 1546664 A1 | 6/2005 |
|---|---|---|
| EP | 1771132 A2 | 4/2007 |
| EP | 1789122 A2 | 5/2007 |
| EP | 2055266 A2 | 5/2009 |
| EP | 2012660 B1 | 9/2009 |
| EP | 2131913 A1 | 12/2009 |
| EP | 2163216 A2 | 3/2010 |
| EP | 2163217 A2 | 3/2010 |
| EP | 2185107 A1 | 5/2010 |
| EP | 2470248 | 3/2011 |
| EP | 2399550 A1 | 12/2011 |
| EP | 2473123 A1 | 7/2012 |
| EP | 2494419 A2 | 9/2012 |
| EP | 2512577 A2 | 10/2012 |
| EP | 1796597 B1 | 1/2013 |
| WO | WO198809188 A | 12/1988 |
| WO | WO199306878 A | 4/1993 |
| WO | WO199706973 A | 2/1997 |
| WO | WO199828034 A | 7/1998 |

OTHER PUBLICATIONS

Wilburn (retrieved on Sep. 5, 2017 from: http://www.nursingworld.org/MainMenuCategories/ANAMarketplace/ANAPeriodicals/OJIN/TableofContents/Volume92004/No3Sept04/InjuryPrevention.html; Online Journal of Issues in Nursing. 2004;9(3):9 pages).*

European Search Report issued in EP Application No. 12815179.2, dated Apr. 28, 2015, 6 pages.

Grundfest, Warren S., MD, et al., "Laser Ablation Of Human Atherosclerotic Plaque Without Adjacent Tissue Injury," JACC vol. 5, No. 4, (Apr. 1985), pp. 929-933.

International Search Report and Written Opinion issued in PCT/US2008/082732 dated Dec. 29, 2008, 6 pages.

Merit Medical Systems, Inc. Merit Marquis Flow Switch: Traditional Premarket Notification 510(k). Section 510(k) summary, Jul. 1, 2011, 6 pages.

MeritMedical Flow Control Switch- Instructions for Use. Merit Medical Systems, Inc. 2 pages. This document and/or corresponding part was potentially available prior to the filing date of the present application and/or the relevant priority date(s) of the present application.

MeritMedical: Flow Control Switch Confidently Control Fluid Flow, Merit Medical Systems, Inc., 2 pages. This document and/or corresponding part was potentially available prior to the filing date of the present application and/or the relevant priority date(s) of the present application.

NAMIC@ Fluid Management: Constructed for Confidence. Configured for Care. Systems for Cardiac Catheterization Labs. Navilyst Medical, Inc. 2009, 11 pages.

Office Action for U.S. Appl. No. 12/061,430 dated Dec. 19, 2008, 10 pages.

Office Action for U.S. Appl. No. 12/176,886 dated Jan. 25, 2013, 10 pages.

Office Action for U.S. Appl. No. 12/176,886 dated Sep. 26, 2012, 12 pages.

Product Catalogue: Peripheral Interventions Vascular Surgery, Boston Scientific, 147 pages, 2007.

Qosina Part No. 97337 (Inline Flow Control Switch). Dec. 1, 2012, 1 page.

U.S. Appl. No. 12/254,254, filed Oct. 20, 2008 entitled Liquid Light-Guide Catheter With Optically Diverging Tip.

U.S. Appl. No. 12/061,430, filed Apr. 2, 2008 entitled Laser With Tapered Waveguide.

* cited by examiner

TAPERED LIQUID LIGHT GUIDE

CROSS-REFERENCE TO RELATED APPLICATIONS

This application is a continuation of U.S. patent application Ser. No. 14/613,949, filed Feb. 4, 2015, now U.S. Pat. No. 9,339,337, titled TAPERED LIQUID LIGHT GUIDE, which is a continuation of U.S. patent application Ser. No. 12/176,886, filed Jul. 21, 2008, now U.S. Pat. No. 8,979,828, titled TAPERED LIQUID LIGHT GUIDE. Each of the above documents are hereby incorporated herein by reference in their entireties for all that they teach and for all purposes.

BACKGROUND

This disclosure relates in general to liquid light guides and, but not by way of limitation, to liquid light guides used in conjunction with a laser catheter among other things.

Catheters containing optical fibers transmit energy to irradiate internal parts of the body for diagnostic and therapeutic purposes. There are many medical applications in which it is desirable to deliver energy, such as laser energy, through an optical fiber or similar waveguide device disposed in a body cavity for treatment or diagnosis. These include, among others, the ablation of tissue such as plaque, calcium, and tumors, the destruction of calculi, and the heating of bleeding vessels for coagulation. Some ablation targets, such as, calcified endovascular lesions, for example, can be especially difficult to ablate. The lasers used may produce either pulsed or continuous-wave light of wavelengths ranging from the ultra-violet to the infra-red.

BRIEF SUMMARY

A catheter tip is provided according to one embodiment. The catheter tip may comprise a distal end, a proximal end, and tubular walls. The distal end includes a distal aperture with a distal inside diameter, and the proximal end includes a proximal aperture with a proximal inside diameter. The proximal inside diameter may be greater than the distal inside diameter. The proximal end comprises attachment means configured to couple the proximal end with a distal end of a laser catheter. The tubular walls may include at least an inside taper from the proximal end to the distal end such that the inner tubular walls generally taper from the proximal inside diameter to the distal inside diameter. Moreover, the tubular walls may be configured to direct at least a liquid medium, for example, a biocompatible solution, toward the distal aperture. In some embodiments, the tubular walls comprise a material with an index of refractive approximately less than or equal to the index of refraction of the liquid medium.

A tapered support sheath is also provided according to another embodiment. The tapered support sheath may include a proximal end including a proximal aperture configured to receive a laser catheter, a distal end including a distal aperture, and an elongated tubular structure. In some embodiments, the inside diameter of the distal aperture is less than the inside diameter of the proximal aperture. The elongated tubular structure may include an inner lumen that extends from the proximal end to the distal end and may include a taper. The elongated tubular structure may also be configured to support a laser catheter within at least a portion of the inner lumen such that the laser catheter directs light toward the distal aperture. In other embodiments, the elongated tubular structure may be configured to allow a liquid medium to flow toward the distal end within the inner lumen. The tapered support sheath may also include a liquid medium infusion port at or near the proximal end of the sheath.

A device for increasing the energy density of light emanating from a laser catheter is also disclosed according to one embodiment. The device may include a proximal end, a distal end, an elongated tubular structure, coupling means, directing means and concentrating means. The elongated tubular structure may include an inner lumen and extend from the proximal end to the distal end. The elongated tubular structure may be configured to allow a liquid medium to flow through the inner lumen toward the distal end. The coupling means may include means for coupling the device with the laser catheter. The directing means may include means for directing light through at least a portion of the device toward a target. The concentrating means may include means for increasing the energy density of the light beam exiting the device compared with the energy density of the light beam entering said device.

A tapered liquid light guide is disclosed according to another embodiment that includes a distal end with a distal aperture, a proximal end with a proximal aperture, and a body. The cross-section of the proximal aperture is greater than the cross-section of the distal aperture. The body may include an inner lumen; a portion of which is tapered. At least a portion of the inner lumen includes a material with an index-of-refraction which is lower than the inner liquid medium. The inner lumen is also configured to allow a liquid medium to flow toward the distal end.

A tapered liquid light guide is disclosed according to another embodiment that includes a distal end with a distal aperture, a proximal end with a proximal aperture, and a body. The cross-section of the distal aperture is greater than the cross-section of the proximal aperture. The body may include an inner lumen; a portion of which is tapered. At least a portion of the inner lumen includes a material with an index-of-refraction which is lower than the inner liquid medium. The inner lumen is also configured to allow a liquid medium to flow toward the distal end.

Further areas of applicability of the present disclosure will become apparent from the detailed description provided hereinafter. It should be understood that the detailed description and specific examples, while indicating various embodiments, are intended for purposes of illustration only and do not limit the scope of the disclosure.

Figure 1:
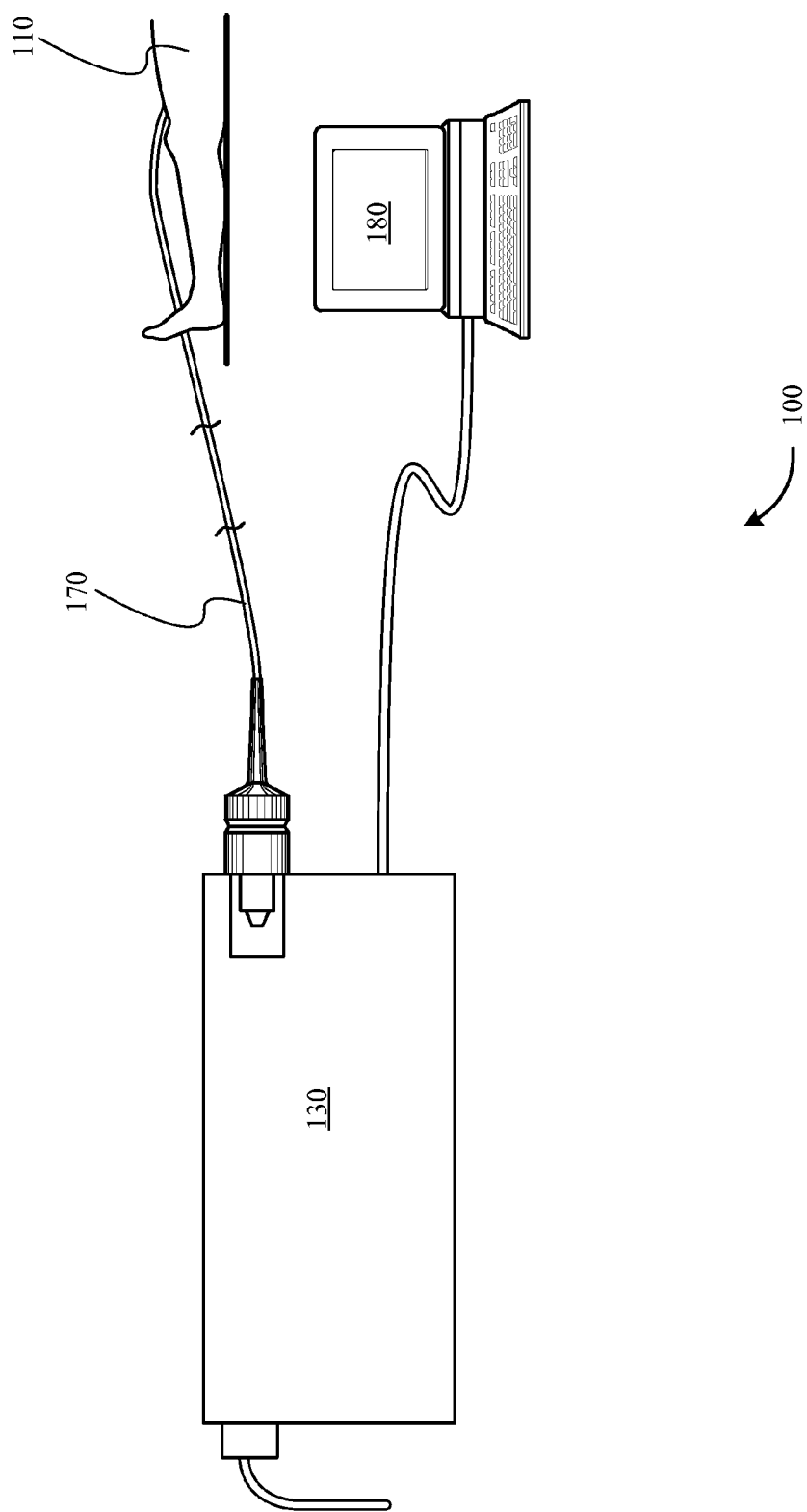
FIG. 1 shows a laser catheter system according to one embodiment.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the disclosure. Rather, the ensuing description of the preferred exemplary embodiment (s) will provide those skilled in the art with an enabling description for implementing a preferred exemplary embodiment. It should be understood that various changes may be made in the function and arrangement of elements without departing from the spirit and scope as set forth in the appended claims.

Embodiments described throughout this disclosure provide for tips, sheaths, catheters, and/or devices that increase the energy density of a laser catheter. Some embodiments use tapered liquid light guides that decrease the beam cross-section of laser light in order to increase the energy density. Such energy density increases may be useful for ablating stubborn lesions, occlusions, obstructions, etc. Moreover, many of the embodiments are directed to devices that may be accessories to a standard laser catheter. For example, various embodiments include detachable and/or replaceable catheter tips and/or sheaths.

A tapered catheter tip is provided according to one embodiment. Such a tapered catheter tip may be coupled with a laser catheter. The taper provides a decrease in the laser spot size and, therefore, an increase in the energy density of laser light. Such tips, in one embodiment, may be constructed of material with an index of refraction which is lower than the liquid medium on the inner lumen at the tip in order to induce internal reflection from within the liquid core. In another embodiment, a tip may be constructed of a material that provides low light attenuation. In some embodiments the laser catheter may provide light in the ultraviolet range. Moreover, the tapered catheter tip may direct a liquid medium from the proximal end of the tip toward the distal end of the tip.

In use, a user may be performing laser ablation within patient using a liquid light guide laser catheter. In this example, the laser catheter may operate with 308 nm UVB light and the laser catheter may use a range of solutions such as NaCl solution as the liquid light guide medium. At some point in the procedure the doctor may encounter a target that is difficult to ablate with the laser catheter, such as, calcified endovascular lesions. In such a case, an increased laser density may provide better ablation. Accordingly, the doctor may remove the laser catheter, attach a tapered catheter tip. The tapered catheter tip narrows the spot size of the laser light emanating from the laser catheter while transmitting roughly the same laser energy. The doctor may then reinsert the laser catheter and ablate the difficult target using the tapered tip. Following ablation, the doctor may remove the tip or continue ablation with the tapered tip.

Some embodiments provide a tapered catheter sheath. Such a catheter sheath may be an elongated tubular structure that accepts a laser catheter through much of the elongated portion thereof. In other embodiments the elongated tubular structure accepts a laser catheter through all, most of all, or a portion thereof. In some embodiments the catheter sheath is tapered at the distal end to decrease the spot size of the laser light. In other embodiments the catheter sheath may include an infusion port that provides biocompatible fluid delivery through the sheath toward the distal end of the sheath. In another embodiment, a sheath may be constructed of a material that provides low attenuation of light. In some embodiments the sheath or at least a tapered portion of the sheath may be constructed of material with a low index of refraction in order to induce total internal reflection. In some embodiments the laser catheter may provide light in the ultraviolet range.

FIG. 1 shows a laser catheter system 100 according to one embodiment. A laser 130 is shown coupled with a user interface 180. In this embodiment the user interface 180 is computer programmed to control the laser 130. The laser, for example, may be an excimer laser. The laser, for example, may also produce light in the ultraviolet range. The laser is connected with a catheter 170 that may be inserted into a vessel of the human body 110. The laser catheter system 100 may employ one or more tapered waveguides that guide laser light from the laser 130 through the catheter 170 toward a target.

Figure 2:
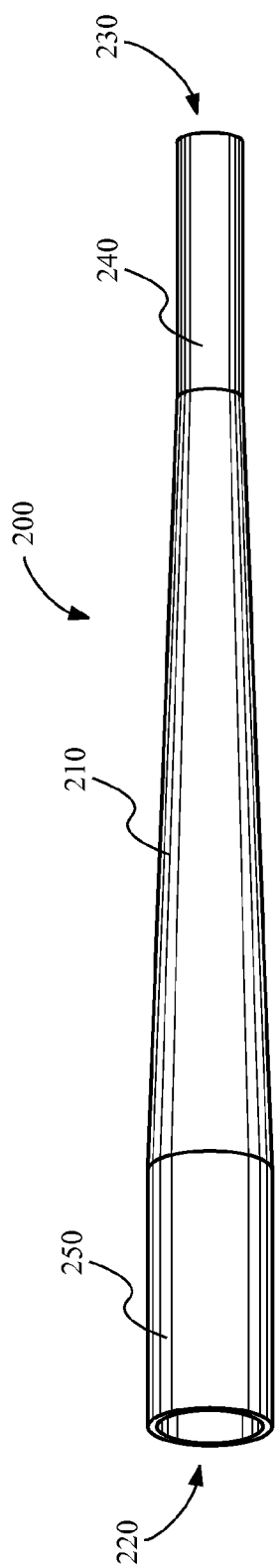
FIG. 2 shows a tapered liquid light guide tip according to one embodiment.

FIG. 2 shows a tapered liquid light guide tip 200 according to one embodiment. The liquid light guide tip 200 includes a distal end 230 and a proximal end 220. In this embodiment both the distal end 230 and the proximal end 220 include apertures. As shown in the figure the tip includes a tapered portion 210 between the proximal end 220 and the distal end 230. In some embodiments, the proximal end 220 of the tapered liquid light guide tip may be coupled with a laser catheter, a liquid light guide 200, or both.

Figure 3:
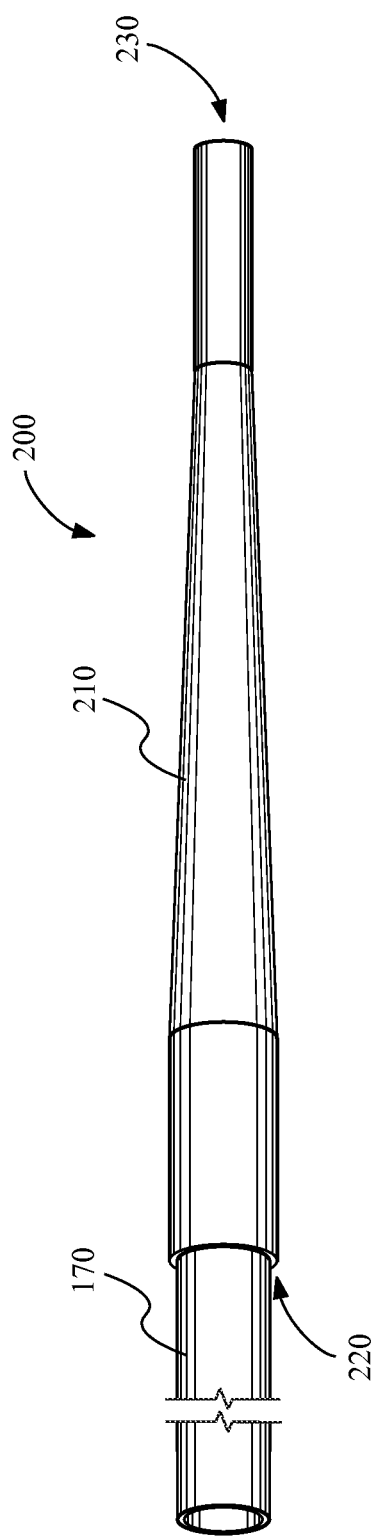
FIG. 3 shows a tapered liquid light guide tip coupled with a laser catheter according to one embodiment.

FIG. 3 shows the proximal end 220 of a tapered liquid light guide tip 200 coupled with a laser catheter 170 according to one embodiment. Only a portion of the laser catheter 170 is shown. When coupled with a laser catheter 170, the liquid light guide tip 200 may direct laser light with a more concentrated spot beam toward a target from the distal end 230. In doing so, the energy density of the light incident on a target from the laser catheter 170 through the liquid light guide tip 200 is increased due to the decrease in spot size. The laser catheter 170 may also provide a biocompatible fluid that flows through the liquid light guide tip 200 from the proximal end 220 toward the distal end 230. In order to decrease the spot size of the laser beam through the tip, total internal reflection must be maintained through the taper 210 of the liquid light guide tip 200. Total internal reflection can be maintained when the biocompatible fluid has a index of refraction greater than the index of refraction of the lining of the tubing.

The biocompatible fluid, in some embodiments, may include a saline solution. In other embodiments the biocompatible fluid may include $MgCl_2$, NaCl, CaCl, etc. In other embodiments the biocompatible fluid may include a solution comprising, for example, Ca, Mg, Mn, Ni, Cl, and/or Co. In some embodiments, the biocompatible fluid may include lactated Ringer's solution. The lactated Ringer's solution, for example, may come from sodium chloride (NaCl), sodium lactate ($NaC_3H_5O_3$), calcium chloride ($CaCl_2$), and/or potassium chloride (KCl). Those of skill in the art will recognize that other combinations of salts may be used. In some embodiments, magnesium chloride and lactated Ringer's solution have good biocompatibility (e.g., low toxicity) as well as good light transmission characteristics at the 308 nm wavelength. The biocompatible fluid may be tailored to the wavelength of light produced by the laser. For example, waveguides including a biocompatible fluid of approximately 15% to approximately 60% w/w $CaCl_2$ transmit light well in the infrared, but only partially in the ultraviolet region. Also, such waveguides generally do not transmit well below 250 nm. There are many types of biocompatible fluids that may be used without limitation. Moreover, embodiments described herein are not limited to specific biocompatible fluid.

The body and/or walls of the tapered liquid light guide tip 200 may comprise any low index material without limitation. For example, a material with an index or refraction below the index of refraction of water, approximately 1.4 at the 308 nm wavelength. These materials may include, for example, Teflon AF2400 tubing made by DuPont. In other embodiments, the walls may include any fluoropolymer, such as, for example, Hyflon® PFA or MFA, FEP, KEL-F, Teflon PFA, Tefzel, Fluon, Tedlar, ECTFE, PVDF, PCTFE, FFKM, Kalrez, Viton, Krytox, and 3M THV-500. Polyethylene, PVC, polycarbonate and/or other plastics may be used in some embodiments.

The tapered liquid light guide tip 200 may include portions without a taper. For example, as shown in FIG. 2 the tip 200 may include a extended portion 250 near the proximal end and/or a extended portion 240 near the distal end. While the extended portion 250 and/or the distal aperture is shown with a circular cross section, any shape may be used. For example, the cross section may be oval or polygon shaped. Moreover, in another embodiment the distal end may taper directly to the distal aperture 230 without a substantially extended portion. In another embodiment, the tip may be substantially cone shaped. In such an embodiment, the tip may have substantially no extended portions.

Figure 4:
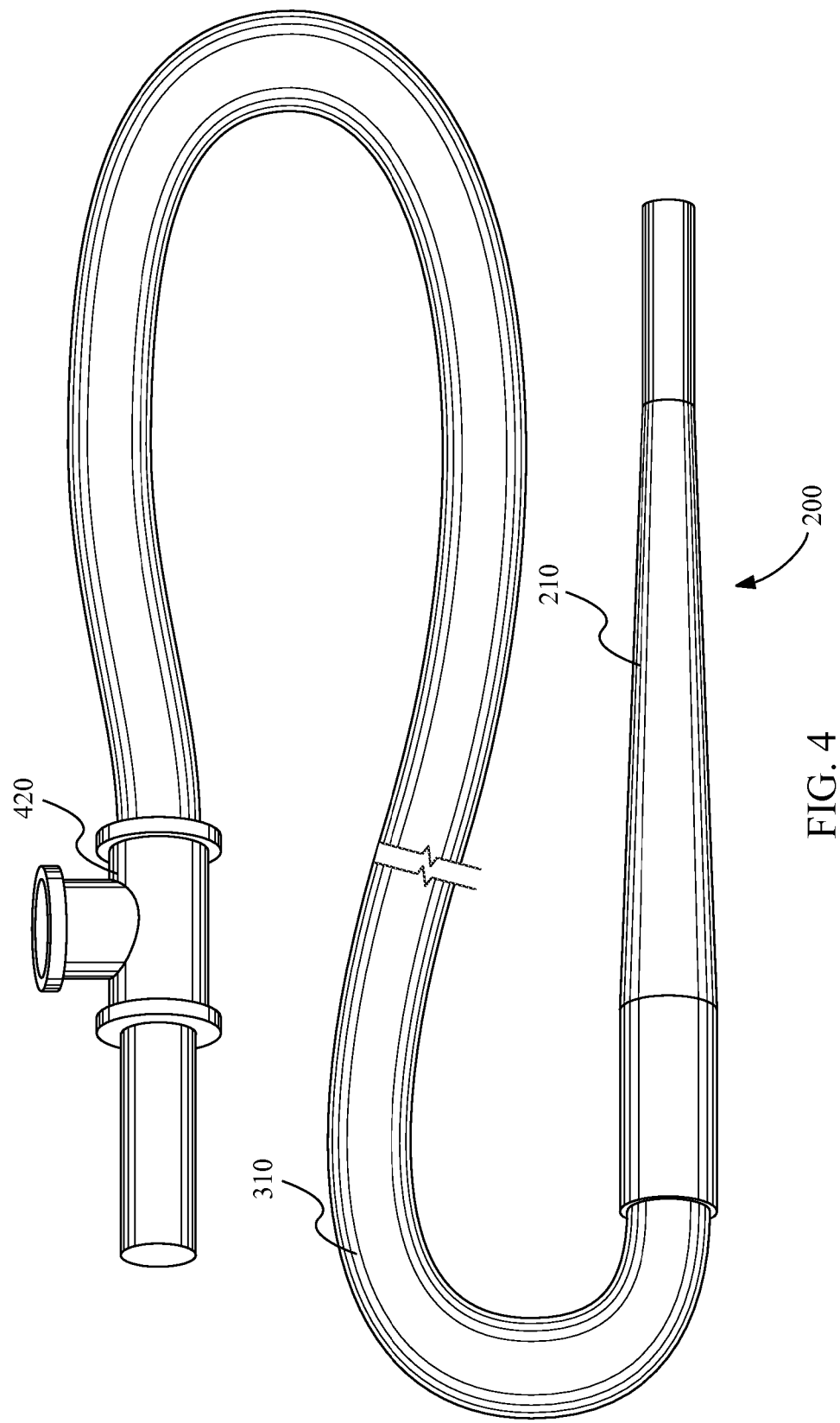
FIG. 4 shows a liquid light guide catheter coupled with a tapered liquid light guide tip according to one embodiment.

FIG. 4 shows a liquid light guide catheter 310 coupled with a tapered liquid light guide tip 200 according to one embodiment. The liquid light guide catheter 310 also includes an infusion port 420 for introducing a biocompatible material into the laser catheter 310. The biocompatible material may act as a light guide within the laser catheter that channels light from the proximal end through toward the distal end. The tapered liquid light guide tip 200 includes a tapered portion 210.

Figure 5A:
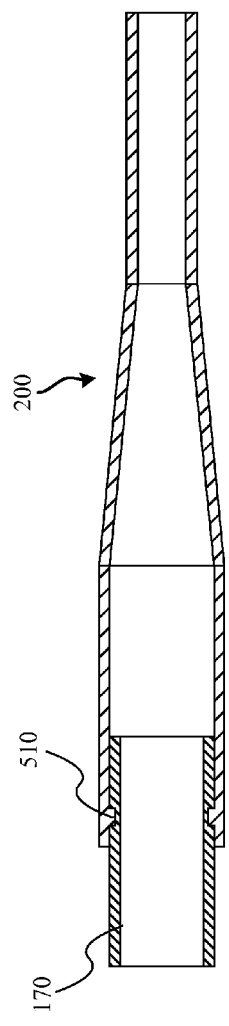
FIGS. 5A-5C show tapered liquid light guide tips with various attachment mechanisms according to various embodiments.
Figure 5B:
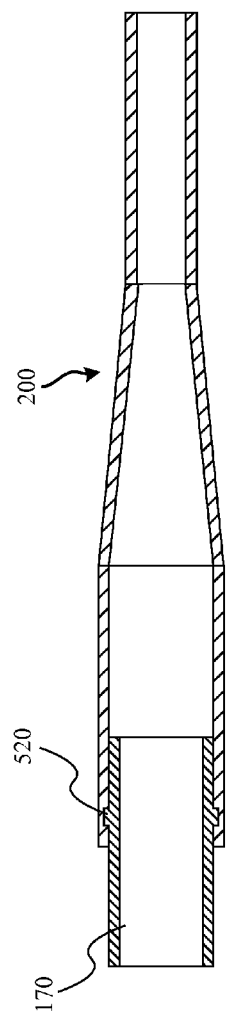
Figure 5C:
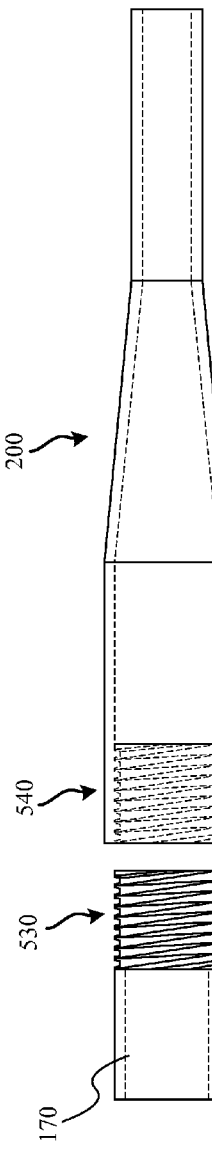

FIGS. 5A-5C show tapered liquid light guide tips with various attachment mechanisms according to various embodiments. FIG. 5A shows an attachment mechanism such that a ring 510 on the inside of the tip catches a grove on the catheter according to one embodiment. In some embodiments, at least a portion or all of the attachment mechanism comprises a shape-memory material that shrinks when heated to about the body temperature. Shrinking may more tightly secure the tip to the laser catheter when used within a body. In FIG. 5B a ring 520 is on the exterior of the laser catheter and the grove is on the interior of the tip 200 according to another embodiment. FIG. 5C shows the tip with threads 540 on the interior and the laser catheter with threads 530 on the exterior. Of course, the threads may be on the exterior of the tip and the interior of the laser catheter according to another embodiment. Various other attachment mechanisms may also be used without deviating from the spirit and scope of this disclosure. For example, clips, detents, rings, washers, pins, bushings, a-rings, etc., may be used as part of the attachment mechanism. In some embodiments, the tapered liquid light guide tip may be attached using an X-Ray contrast medium, a sticky material or any adhesive.

Figure 6:
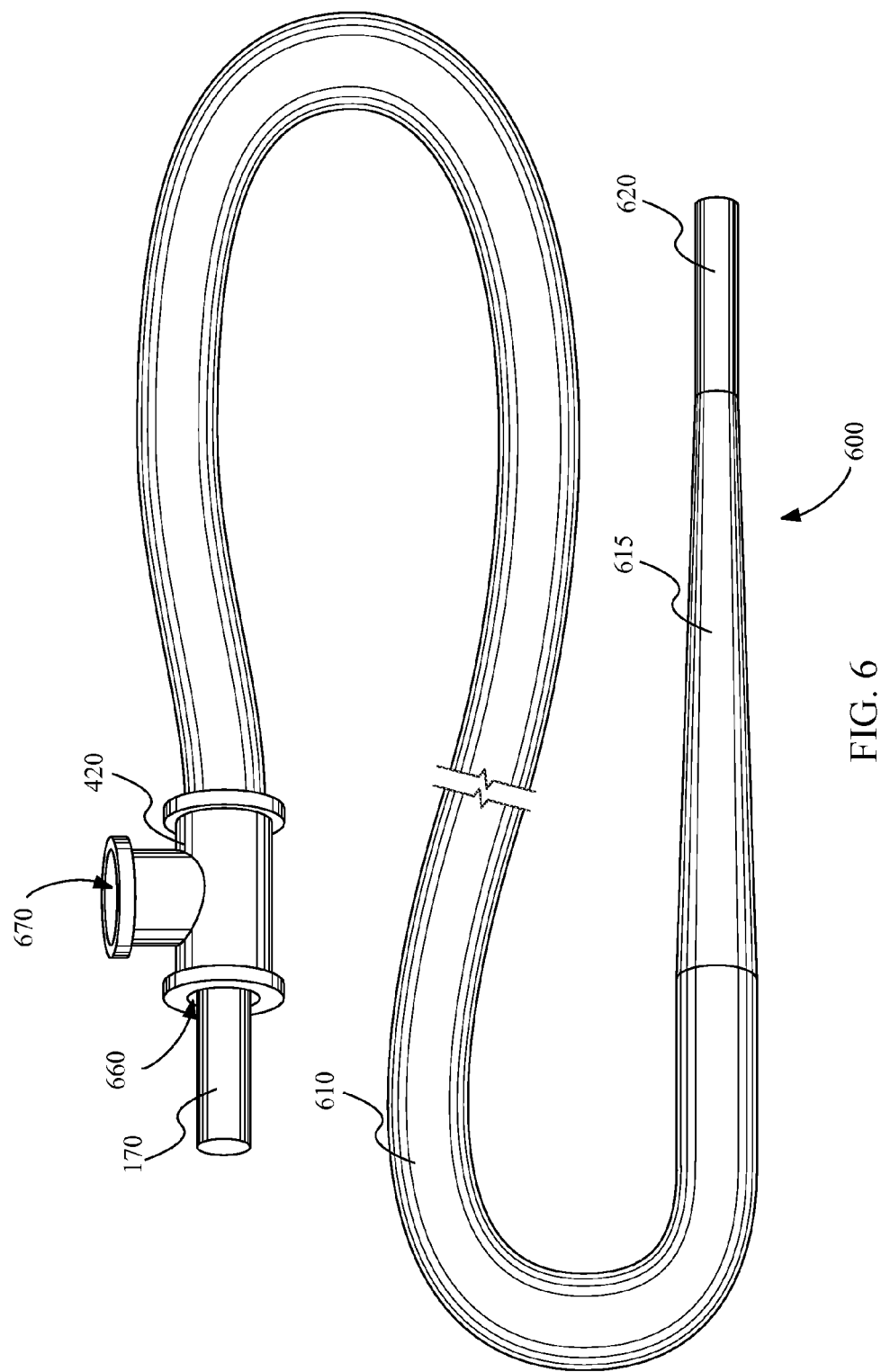
FIG. 6 shows a tapered liquid light guide sheath according to one embodiment.

FIG. 6 shows a tapered liquid light guide sheath 600 according to another embodiment. The liquid light guide sheath 600 may include an elongated tubular body 610, a tapered portion 615, a distal aperture, an inner lumen, and an infusion port 420. The infusion port 640 includes a catheter port 660 that receives a laser catheter 170 or other light channeling device. The catheter port is configured to allow a catheter, such as a laser catheter, to be fed into the inner lumen of the sheath 600. The sheath 600 may also include a fluid port 670 that may be coupled, for example, with a biocompatible fluid delivery device. The fluid port 670 may receive biocompatible fluid that flows through the inner lumen of the sheath 600. The biocompatible fluid may be used as a light guide within portions of the sheath. In some embodiments, the liquid light guide sheath may include a distal extended portion 620, while in other embodiments the sheath tapers substantially directly to the distal aperture.

The tapered liquid light guide sheath 600 may be used to direct laser light from a catheter and biocompatible fluid toward a target. The laser catheter 170 may slide within the inner lumen from the infusion port 420 toward the distal end. Portions of the sheath 600 may act as a liquid light guide directing light from the laser catheter through a distal aperture toward a target. Accordingly, in some embodiments, portions or some portions of the tapered liquid light guide sheath 600 may comprise a low index material and/or a low attenuation material. The type of material chosen as well as the type of biocompatible fluid used within the light guide may be chosen based on the wavelength of light produced by the laser catheter.

Specific details are given in the above description to provide a thorough understanding of the embodiments. However, it is understood that the embodiments may be practiced without these specific details. For example, circuits, structures, and/or components may be shown in block diagrams in order not to obscure the embodiments in unnecessary detail. In other instances, well-known circuits, processes, algorithms, structures, components, and techniques may be shown without unnecessary detail in order to avoid obscuring the embodiments.

While the principles of the disclosure have been described above in connection with specific apparatuses and methods this description is made only by way of example and not as limitation on the scope of the disclosure.

What is claimed is:

1. A tapered liquid light guide sheath configured to increase energy density of light emanating from a laser catheter, the tapered liquid light guide sheath comprising:
   a proximal end including a proximal aperture having a first cross-section, the proximal aperture being configured to slidably receive the laser catheter;
   an elongated tubular body coupled to the proximal end and configured to slidably receive the laser catheter from the proximal aperture;
   a distal end including a distal aperture having a second cross-section, the second cross-section being smaller than the first cross-section;
   a tapered portion coupled between the elongated tubular body and the distal end, the tapered portion including an inner lumen having a longitudinal axis therethrough and tapering from the elongated tubular body to the distal end, wherein the inner lumen toward the elongated tubular body is larger than the inner lumen toward the distal end, wherein the tapered portion is configured to direct light received from the laser catheter toward the distal aperture, wherein the tapered portion is configured to allow a liquid medium to flow toward the distal end within the inner lumen, and wherein the inner lumen is constructed from a flexible material configured to induce internal reflection of light within the liquid medium; and,
   an extended portion extending longitudinally from the tapered portion and including the inner lumen and the distal end, wherein the extended portion has a circular cross-section perpendicular to the longitudinal axis equal to the second cross-section, wherein the circular cross-section is the same along the length of the extended portion.

2. The tapered liquid light guide sheath according to claim 1, wherein the material comprises a plastic.

3. The tapered liquid light guide sheath according to claim 2, wherein the plastic comprises at least one of a fluoropolymer, polycarbonate, polyethylene, and polyvinyl chloride.

4. The tapered liquid light guide sheath according to claim 1, wherein the material has an index of refraction below 1.4 at a wavelength of 308 nm.

5. The tapered liquid light guide sheath according to claim 1, further comprising an infusion port at the proximal end, the infusion port including the proximal aperture and a fluid port for receiving the liquid medium.

6. The tapered liquid light guide sheath according to claim 1 further comprising the liquid medium, wherein the liquid medium comprises a biocompatible solution.

7. The tapered liquid light guide sheath according to claim 1 further comprising the liquid medium, wherein the liquid medium comprises a solution comprising a salt selected from the group consisting of $MgCl_2$, NaCl and CaCl.

8. The tapered liquid light guide sheath according to claim 1 further comprising the liquid medium, wherein the liquid medium comprises a salt solution.

9. A tapered liquid light guide sheath configured to increase energy density of light emanating from a laser catheter, the tapered liquid light guide sheath comprising:
a distal end with a distal aperture having a distal cross-section;
a proximal end with a proximal aperture having a proximal cross-section, the proximal cross-section being greater than the distal cross-section, and the proximal aperture being configured to slidably receive the laser catheter;
an elongated tubular body coupled to the proximal end and configured to slidably receive the laser catheter from the proximal aperture;
a tapered body coupled between the distal end and the elongated tubular body, the tapered body including an inner lumen, having a longitudinal axis therethrough, that tapers from the elongated tubular body to the distal end, wherein the tapered body is configured to support the laser catheter within the inner lumen, the inner lumen configured to allow a liquid medium to flow toward the distal end, and wherein the inner lumen is constructed from a flexible material configured to induce internal reflection of light within the liquid medium; and,
an extended portion extending longitudinally from the tapered body and including the inner lumen and the distal end, wherein the extended portion has a circular cross-section perpendicular to the longitudinal axis equal to the distal cross-section, wherein the circular cross-section is the same along the length of the extended portion.

10. The tapered liquid light guide sheath according to claim 9, wherein the material comprises a plastic.

11. The tapered liquid light guide sheath according to claim 10, wherein the plastic comprises at least one of a fluoropolymer, polycarbonate, polyethylene, and polyvinyl chloride.

12. The tapered liquid light guide sheath according to claim 9, wherein the material has an index of refraction below 1.4 at a wavelength of 308 nm.

13. The tapered liquid light guide sheath according to claim 9, further comprising an infusion port at the proximal end, the infusion port including the proximal aperture and a fluid port for receiving the liquid medium.

14. The tapered liquid light guide sheath according to claim 9 further comprising the liquid medium, wherein the liquid medium comprises a biocompatible solution.

15. The tapered liquid light guide sheath according to claim 9 further comprising the liquid medium, wherein the liquid medium comprises a solution comprising a salt selected from the group consisting of $MgCl_2$, NaCl and CaCl.

16. The tapered liquid light guide sheath according to claim 9 further comprising the liquid medium, wherein the liquid medium comprises a salt solution.

17. A tapered liquid light guide sheath configured to increase energy density of light emanating from a laser catheter, the tapered liquid light guide sheath comprising:
a distal end with a distal aperture;
a proximal end with a proximal aperture configured to slidably receive the laser catheter;
an elongated tubular body coupled to the proximal end and configured to slidably receive the laser catheter from the proximal aperture;
a tapered body coupled between the distal end and the elongated tubular body, the tapered body including an inner lumen having a longitudinal axis therethrough, wherein the inner lumen tapers from a first cross-section adjacent the elongated tubular body to a second cross-section adjacent the distal end, wherein the first cross-section is larger than the second cross-section, wherein the tapered body is configured to support the laser catheter within the inner lumen, the inner lumen configured to allow a liquid medium to flow toward the distal end, and wherein the inner lumen is constructed from a flexible material configured to induce internal reflection of light within the liquid medium, wherein the material has an index of refraction below 1.4; and,
an extended portion extending longitudinally from the tapered body and including the inner lumen and the distal end, wherein the extended portion has a circular cross-section perpendicular to the longitudinal axis equal to the second cross-section, wherein the circular cross-section is the same along the length of the extended portion.

18. The tapered liquid light guide sheath according to claim 17, wherein the material comprises a plastic.

19. The tapered liquid light guide sheath according to claim 18, wherein the plastic comprises at least one of a fluoropolymer, polycarbonate, polyethylene, and polyvinyl chloride.

* * * * *